(12) United States Patent
Ayliffe et al.

(10) Patent No.: US 8,072,603 B2
(45) Date of Patent: Dec. 6, 2011

(54) FLUORESCENCE-ACTIVATED CELL DETECTOR

(75) Inventors: Harold E. Ayliffe, Woodinville, WA (US); Curtis S. King, Kirkland, WA (US)

(73) Assignee: E I Spectra, LLC, Woodinville, WA (US)

( * ) Notice: Subject to any disclaimer, the term of this patent is extended or adjusted under 35 U.S.C. 154(b) by 302 days.

(21) Appl. No.: 12/378,757

(22) Filed: Feb. 19, 2009

(65) Prior Publication Data

US 2009/0189088 A1 Jul. 30, 2009

Related U.S. Application Data

(63) Continuation-in-part of application No. 11/701,711, filed on Feb. 2, 2007, now Pat. No. 7,515,268.

(60) Provisional application No. 60/764,697, filed on Feb. 2, 2006.

(51) Int. Cl.
*G01N 21/64* (2006.01)

(52) U.S. Cl. ............. 356/417; 356/246; 435/288.7; 436/172; 250/458.1; 250/461.2

(58) Field of Classification Search .......... 356/417, 356/246
See application file for complete search history.

(56) References Cited

U.S. PATENT DOCUMENTS

| | | | |
|---|---|---|---|
| 3,910,702 A | 10/1975 | Corll | |
| 4,130,754 A | 12/1978 | Fosslien | |
| 4,164,870 A | 8/1979 | Scordato et al. | |
| 4,488,814 A | 12/1984 | Johnson | |
| 4,873,875 A | 10/1989 | Cork | |
| 5,516,564 A | 5/1996 | Root et al. | |
| 5,695,092 A | 12/1997 | Schrandt | |
| 6,285,807 B1 | 9/2001 | Walt et al. | |
| 6,396,584 B1 | 5/2002 | Taguchi et al. | |
| 6,663,353 B2 | 12/2003 | Lipscomb et al. | |
| 7,223,371 B2 | 5/2007 | Hayenga et al. | |
| 2002/0061260 A1 | 5/2002 | Husar | |
| 2003/0036206 A1* | 2/2003 | Chien et al. | 436/180 |
| 2003/0180965 A1 | 9/2003 | Yobas et al. | |
| 2006/0073609 A1 | 4/2006 | Shimizu | |

* cited by examiner

*Primary Examiner* — F. L. Evans
(74) *Attorney, Agent, or Firm* — Brian C. Trask

(57) ABSTRACT

An apparatus for detecting particles of interest that are dispersed in a fluid mix, which typically includes other particles. The apparatus typically is associated with an interrogation platform arranged to operate in harmony with an opaque member having an orifice sized to promote single-file travel of the particles there-through. A currently preferred embodiment includes a light pipe configured to impinge stimulation-radiation substantially transverse to a direction of fluid flow through the opaque member. Particles of interest may be tagged using antibody-binding, fluorescing molecules. Stimulation radiation from the source causes the tagged particles to undergo a Stokes-shift emission of fluorescence. The resulting fluorescence is detected by the radiation detector and indicates passage of the particles of interest. One workable opaque member is advantageously included in a thin film assembly carried on a removable and disposable card that is adapted for reception in the interrogation platform.

20 Claims, 16 Drawing Sheets

US 8,072,603 B2

FLUORESCENCE-ACTIVATED CELL DETECTOR

RELATED APPLICATIONS

This application is a continuation-in-part of U.S. utility application Ser. No. 11/701,711, filed on Feb. 2, 2007 now U.S. Pat. No. 7,515,268 and claims the benefit under 35 U.S.C. 119(e) of the filing date of Provisional Application Ser. No. 60/764,697, filed Feb. 2, 2006, for "FLUORESCENCE-ACTIVATED CELL DETECTOR", the entire disclosure of which is hereby incorporated by reference as though set forth herein in its entirety.

BACKGROUND

1. Field of the Invention

This invention relates to optically-based evaluation of particles suspended in a fluid carrier medium. It is particularly directed to an improved apparatus and method for carrying out interrogation of particles by applying radiation to such particles and detecting a shift in wavelength of radiation emitted by selected ones of those particles.

2. State of the Art

Flow cytometry is a well established technique that is used to determine certain physical and chemical properties of microscopic particles by sensing certain optical properties of the particles. Many books and articles are available detailing aspects of this useful investigational tool. For example, operational principles of, and procedures for use of, modern cytometers are set forth in "Practical Flow Cytometry" by Howard M. Shapiro. Flow cytometry is currently used in a wide variety of applications including hematology, immunology, genetics, food science, pharmacology, microbiology, parasitology and oncology.

In flow cytometry, microscopic particles entrained in a carrier fluid are typically arranged in single-file inside a core stream using hydrodynamic focusing. The particles are then individually interrogated by an optical detection system. The interrogation typically includes directing a light beam from a radiation source, such as a laser, transversely across the focused stream of single-file particles. The light beam is scattered by each particle to produce a scatter profile. The scatter profile may be analyzed by measuring the light intensity at both small and larger scatter angles. Certain physical and/or chemical properties of each particle can then be determined from the scatter profile.

It is also known to apply fluorescing markers to selected particles of interest prior to processing such particles in a cytometer. For example, particles such as blood cells can be "tagged" with fluorescent molecules by using conjugated monoclonal antibodies. The wavelength of the radiation source (typically a laser), is matched to the excitation wavelength of the fluorescing molecule marker. The tagged particles fluoresce in the cytometer when excited by the transversely oriented laser beam. The fluorescence given off by the excited particle can be detected by an appropriately configured detector, which is conventionally mounted transverse to the path of the particles in the interrogation portion of the cytometer. Therefore, cells tagged with fluorescing markers can be easily detected for counting, or other data manipulation.

Unfortunately, flow cytometers are undesirably complex and expensive pieces of equipment. Care must be taken to ensure the machine is set up correctly, and properly calibrated. It would be an advance to provide a robust, inexpensive apparatus that can be used to promote single-file particle travel through an optically based interrogation zone to promote rapid processing of a plurality of different particle-bearing fluid samples.

BRIEF SUMMARY OF THE INVENTION

This invention provides an apparatus for optically-based evaluation of particles suspended in a fluid carrier medium. The apparatus includes a plumbing arrangement adapted to transport particles suspended in a fluid. The apparatus is typically associated with an interrogation platform. The plumbing arrangement is desirably structured to urge transit of particles carried in a fluid in substantially single-file through an interrogation zone. One operable interrogation zone may be located in proximity to a first orifice disposed to provide a first flow path. The orifice may be structured to cause a desired organization of particles flowing therethrough, such as substantially in single-file. Prior to interrogation, the particles of interest are generally tagged with a fluorescing marker of some sort.

A radiation source is disposed to impinge radiation into the interrogation zone. In certain embodiments, the interrogation zone may be disposed on a first side of an opaque member. The opaque member is optional, in certain embodiments. An operable radiation source is arranged to apply primary radiation in a direction along a radiation vector into an interrogation zone effective to excite a first subset of particles passing through the zone operably to cause an emission of fluorescence from a first particle selected from the first subset. A first portion of fluorescence from the excited particle is then available for observation or detection. A radiation detector can therefore be operably arranged for reception and detecting of the fluorescence from the excited particle.

Desirably, the primary or stimulation radiation has a first characteristic wavelength, and the fluorescence has a second characteristic wavelength that is different from the first characteristic wavelength, known as a Stokes shift. Certain embodiments may include a first filter disposed between the radiation source and radiation detector. In such case, the first filter is typically configured and arranged to resist reception of primary radiation by the radiation detector. Sometimes, a second filter may be disposed on the first side of the opaque member. Such second filter would generally be configured and arranged to resist transmission there-through of radiation departing from the first characteristic, or stimulation, wavelength. Certain embodiments may also include a collecting lens disposed on the second side of the opaque member. If present, a collecting lens is typically configured and arranged to urge part of the fluorescence toward a detecting element of the radiation detector. A workable collecting lens may include a fiber optic cable, or a convex focusing lens.

In certain embodiments, the radiation vector from the radiation source may be oriented at an acute angle to a through-axis of the first orifice. Some embodiments are arranged such that radiation is applied at an acute angle between about 15 degrees and about 75 degrees. The goal of applying the primary or stimulation radiation vector at an angle is simply to avoid direct reception of such radiation by the detector. In other words, it is preferred to make substantially the entire detected signal available for signal processing (e.g. to make better use of the gain in the detector). In an alternative, and currently more preferred embodiment, the stimulation radiation is applied substantially transverse to the through-axis of the orifice.

A plumbing arrangement operable in an alternative embodiment constructed according to certain principles of the instant invention is configured to urge transit of particles in substantially single-file through a plurality of orifices. Each such orifice is disposed to provide a respective flow path through the substantially opaque member. A radiation source is arranged to apply primary radiation into a zone associated with the plurality of orifices effective to excite a first subset of particles passing through the zone operably to cause an emission of fluorescence from certain particles selected from the first subset, with fluorescence from certain tagged particles being directed for transmission in a direction from the first side toward a second side of the substantially opaque member. Sometimes, the radiation detector may be operably arranged for reception and detecting of any resulting fluorescence. Other times, multiple detectors are provided, with each such detector being arranged to monitor one or more interrogation zone.

A currently preferred plumbing arrangement comprises structure arranged such that fluid flow through a first orifice is directed approximately orthogonal to fluid flow in a channel disposed immediately downstream of the first orifice. Further, fluid flow through the first orifice is desirably directed approximately orthogonal to fluid flow in a channel disposed immediately upstream of the first orifice. One representative first orifice has a characteristic dimension sized between about 5 microns and about 200 microns. A thickness of the opaque member of a currently preferred embodiment is between about 10 microns and about 300 microns.

One operable opaque member includes a membrane carrying an opaque substance as a first coating disposed on one side thereof. Sometimes, a second opaque layer may also be included as a second coating disposed on a side opposite the one side. The opaque member can also be formed from a substance that is inherently non-transmitting of radiation. In any case, when the plumbing arrangement is carried on a removable cartridge, a radiation transmission window may sometimes be formed through the thickness of the cartridge.

One operable method of using the instant apparatus includes preparing a sample of particles suspended in a fluid carrier medium by mixing a quantity of particles with antibody-bound fluorescently labeled molecules. The sample is then incubated for a period of time sufficient to permit antibody-bound fluorescently labeled molecules to bind to particles of interest in the sample. An interrogation platform is provided to interrogate the sample. A currently preferred platform is configured to operate on a detection zone disposed in association with an orifice configured to provide an organizing flow path for particles of interest. The orifice is desirably sized sufficiently in agreement with a characteristic size of the particles of interest as to promote substantially single-file travel of such particles of interest there-through. The interrogation platform further includes a radiation source disposed to apply interrogation or primary radiation to an interrogation zone. A radiation detector is disposed to detect fluorescence, or secondary radiation. A portion of the sample is then caused to flow through the detection or interrogation zone. The source of radiation is used to impinge primary radiation, having a first characteristic wavelength, into the detection zone operably to excite antibody-bound fluorescently labeled molecules to promote emission there-from of secondary radiation having a second characteristic wavelength. The radiation detector is used to detect the secondary radiation. Subsequent to interrogation, the portion of the sample flows away from the detection zone.

In one sample preparation procedure, incubation occurs at a temperature between about 20 degrees Celsius and about 39 degrees Celsius. In a currently preferred apparatus and method, the opaque member is included in a plumbing arrangement comprising a thin film assembly carried on a removable card. Such plumbing arrangement causes fluid flow away from the detection zone to occur in an essentially orthogonal direction compared to fluid flow through said orifice. Also, the removable card is desirably configured and arranged to interface with structure of the interrogation platform to hold the card in position during an interrogation procedure. Therefore, the method can also include inserting such removable card into operable position in association with the interrogation platform.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

Unless otherwise obvious in context, the term "fluid" will be used in this disclosure to indicate a mixture of fluid and particles entrained in that fluid. In certain cases, the fluid may have electrolytic properties. In this disclosure, "single-file travel" is defined different than literally according to a dictionary definition. For purpose of this disclosure, single-file travel may be defined as an arrangement of particles sufficiently spread apart as to permit reasonably accurate radiological detection of particles of interest.

Figure 1:
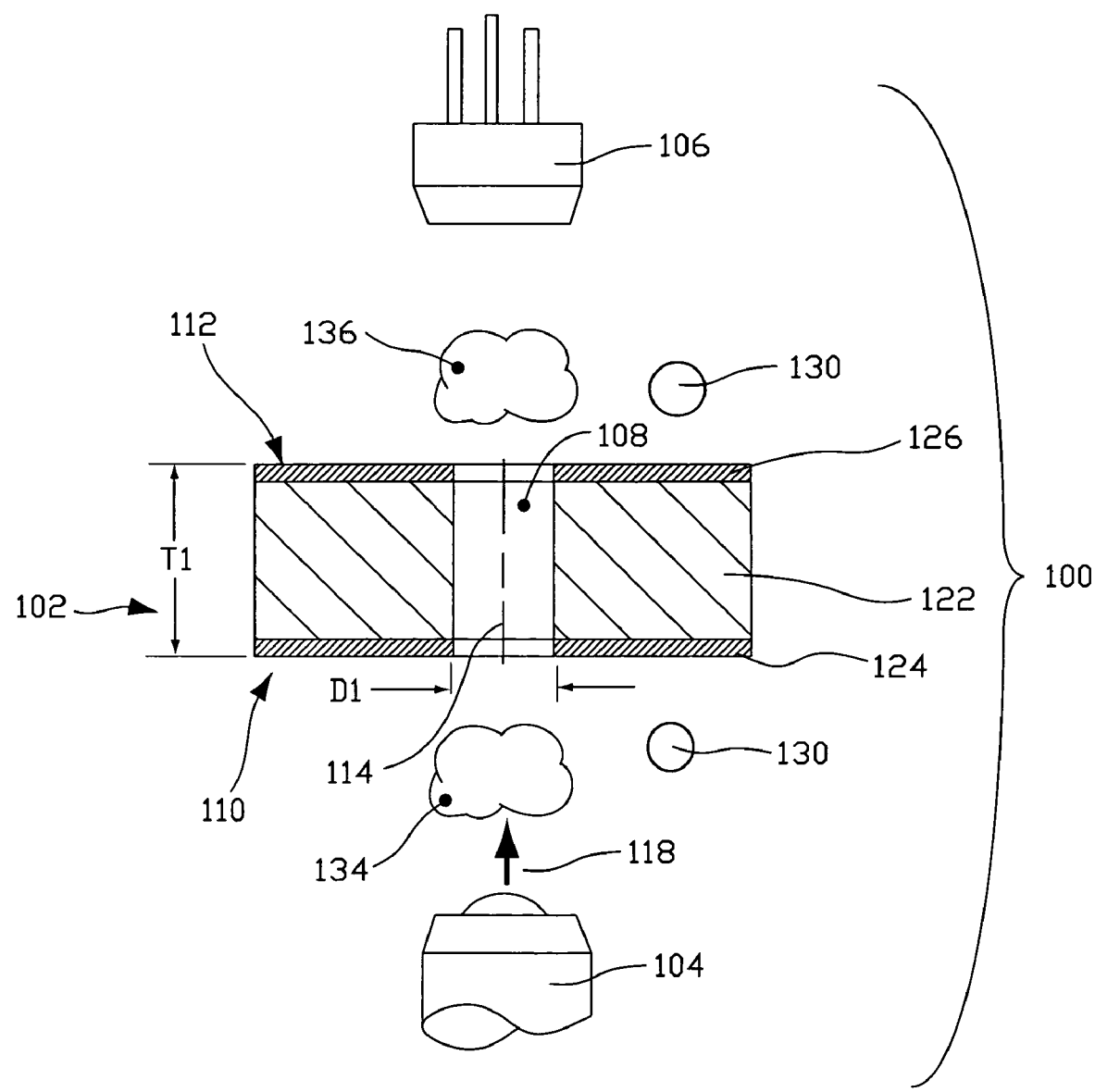
FIG. 1 is a schematic of a cross-section taken through a first embodiment illustrating general principles of operation of the invention.

A schematic illustrating a generalized operable arrangement of structure employed in embodiments structured according to certain principles of the invention is indicated generally at 100 in FIG. 1. As illustrated, embodiment 100 includes an opaque member, generally indicated at 102, disposed between a radiation source 104 and a radiation detector 106. At least one orifice 108 is disposed in opaque member 102 to provide a flow path between a first side, generally indicated at 110, and a second side, generally indicated at 112. Orifice 108 may be characterized as having a through-axis 114 extending between the first and second sides 110 and 112 of opaque member 102, respectively.

Both of the thickness, T1, of an opaque member and characteristic size, D1, of an orifice 108 are typically sized in agreement with a size of a particle of interest to promote single-file travel of the particle through the opaque member, and to have only one particle inside the orifice at a time. In the case where the apparatus is used to interrogate blood cells, the thickness of the opaque member may typically range between about 10 microns and about 300 microns, with a thickness of about 50 microns being currently preferred. The diameter, or other characteristic size of the orifice in such an embodiment, may range between about 5 and 200 microns, with a diameter of about 100 microns being currently preferred in an embodiment adapted to interrogate blood cells.

An operable opaque member 102 functions, in part, to reduce the quantity of unwanted background radiation, including primary radiation 118 (sometimes also called stimulation radiation) that is emitted by source 104, which is received and detected by radiation detector 106. Primary radiation 118 is illustrated as a vector having a direction. Desirably, substantially all of the primary radiation 118 is prevented from being detected by the radiation detector 106. In any case, operable embodiments are structured to resist saturation of the detector 106 by primary radiation 118. As illustrated in the arrangement depicted in FIG. 1, primary radiation 118 may simply pass through orifice 108 for reception by the radiation detector 106. Therefore, as will be further detailed below, certain embodiments may employ one or more selective radiation filters as a measure to control radiation received by detector 106.

The opaque member 102 illustrated in FIG. 1 includes a core element 122, carrying a first coating 124 disposed on first side 110, and a second coating 126 disposed on second side 112. A workable core 122 for use in detecting small sized particles, such as certain blood cells, can be formed from a thin polymer film, such as PET having a thickness of about 0.005 inches. Such polymer material is substantially permeable to radiation, so one or more coatings, such as either or both of coating 124 and 126, is typically applied to such core material. A workable coating includes a metal or alloy of metals that can be applied as a thin layer, such as by sputtering, vapor deposition, or other well-known technique. Ideally, the metal layer should be about 2-times as thick as the wavelength of the primary radiation, e.g. about 1 μm in one operable embodiment. The resulting metallized film may be essentially impervious to transmission of radiation, except where interrupted by an orifice, such as orifice 108. Aluminum is one metal suitable for application on a core 122 as a coating 124 and/or 126. Of course, it is also within contemplation to alternatively use a bare core element that is, itself, inherently resistant to transmission of radiation. For example, a sheet of metal foil may form an effective opaque member in certain operable embodiments.

The apparatus 100 is configured to urge a plurality of particles 130 into substantially single-file travel through orifice 108. A particle 130 typically passes through an excitation zone as the particle approaches, passes through, and departs from the orifice 108. Of note, the direction of particle-bearing fluid flow may be in either direction through orifice 108. In certain cases, an excitation zone may include the through-channel or tunnel defined by orifice 108. An excitation zone may also include a volume indicated by lower cloud 134, which encompasses a volume in which a particle may reside and be in contact with primary radiation. An excitation zone may further include a volume indicated by upper cloud 136, which also encompasses a volume in which a particle may reside and be in contact with primary radiation.

In certain cases, e.g. where there may be a plurality of orifices, the term "zone" may include a plurality of such distributed zones. However, the appropriate meaning of the term "zone" is believed to be aduceable in context. In the excitation zone, primary radiation 108 causes certain particles to fluoresce, thereby emitting radiation at a different wavelength compared to the primary radiation 108 and in substantially all three-dimensions. The fluorescence radiation emitted by those certain particles may then be detected by the radiation detector 106.

Figure 17:
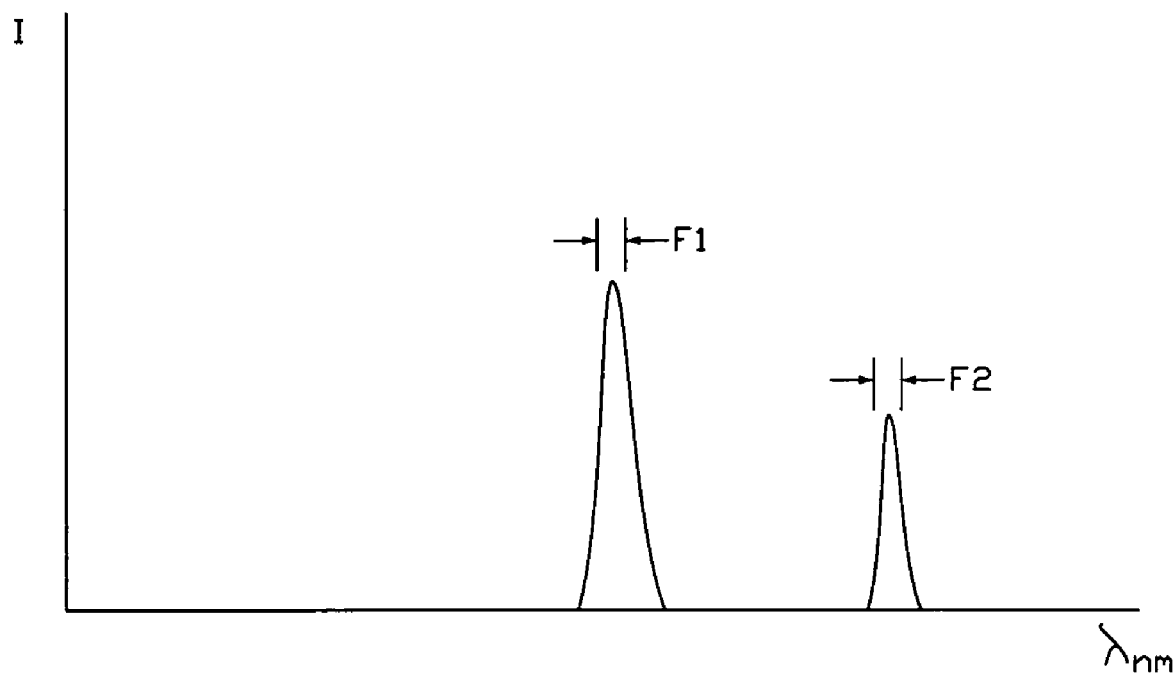
FIG. 17 is a plot illustrating characteristic wavelengths for a representative primary radiation and a resulting fluorescent response.

It should be noted, for purpose of this disclosure, that the term "wavelength" is typically employed not with reference only to a single specific wavelength, but rather to encompass a spread of wavelengths grouped about a characteristic, or representative, wavelength. With reference to FIG. 17, the characteristic wavelength F1 (e.g. excitation wavelength) of the primary radiation 118 is sufficiently different from the characteristic wavelength F2 of the fluorescence (e.g. emission wavelength) to enable differentiation between the two. Furthermore, the difference between such characteristic wavelengths, or Stokes shift, is desirably sufficiently different to enable, in certain embodiments, including a selective-pass filter element between the radiation source 104 and detector 106 effective to block transmission of primary radiation toward the detector, while permitting transmission of the fluorescence through the selective-pass filter to the detector.

With reference again to FIG. 1, the embodiment 100 may essentially be disposed in a suitably sized container that is divided into two portions by the opaque member. Flow of fluid (and particles entrained in that fluid) through the orifice 108 could be controlled by a difference in pressure between the two divided portions. However, it is typically desired to provide more control over the flow path of particles in the vicinity of the orifice 108 than such an embodiment would permit. For example, a clump of particles disposed near an entrance or exit of the orifice 108 could shield a particle of interest from the primary radiation 118 to the extent that fluorescence does not occur, thereby causing a miscount, or preventing detection of such a shielded particle of interest. Also, clumped or stacked particles could shield fluorescence that is emitted from a particle of interest from contact with the detector, thereby reducing detection accuracy.

Figure 2:
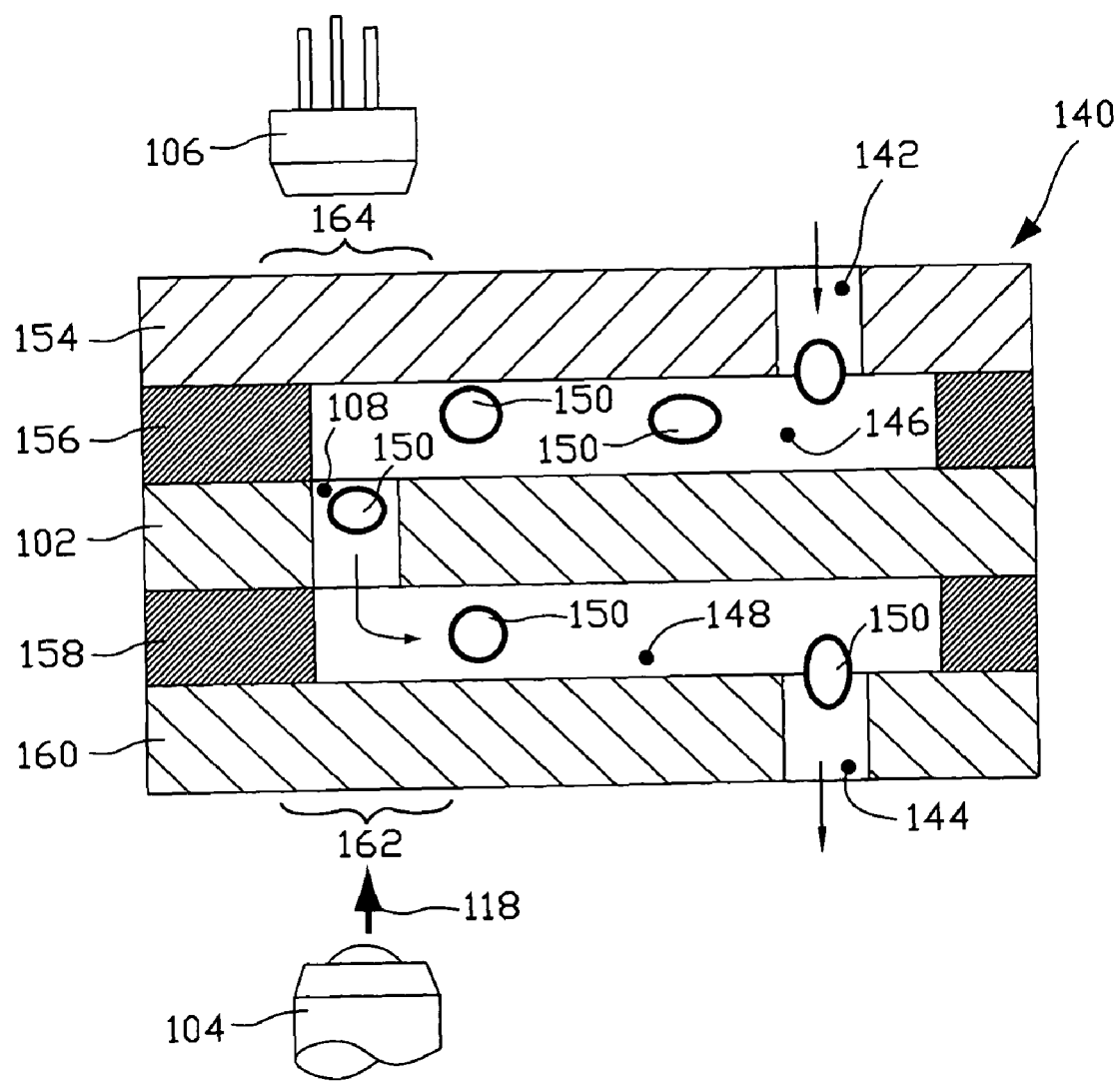
FIG. 2 is a cross-section in elevation illustrating certain details of a workable plumbing arrangement that may be associated with certain structure of an interrogation platform.

One multi-layered embodiment, generally indicated at 140 and illustrated in FIG. 2, provides a plumbing arrangement that is structured to resist particle clumping near the orifice 108, and consequential lack of detection of a particle of interest. Multilayer assembly 140 is structured to urge fluid flow through the orifice 108 in a direction that is essentially orthogonal to fluid flow in channel portions adjacent to, and upstream and downstream of, the orifice 108. Such fluid flow resists stacking of particles in a thickness direction of the plumbing arrangement 140, and thereby reduces likelihood of undetected particles of interest.

Plumbing arrangement 140 includes five layers configured and arranged to form a channel system effective to direct flow of particle bearing fluid from a supply chamber 142, through orifice 108 in an opaque member 102, and toward a waste chamber 144. Desirably, a depth of fluid guiding channels 146 and 148 is sized in general agreement with a size of a particle 150, to resist "stacking" particles near the orifice 108. Fluid can be moved about on the device 140 by imposing a difference in pressure between chambers 142 and 144, or across orifice 108 disposed in opaque member 102. For example, a positive pressure may be applied to the supply chamber 142. Alternatively, a negative pressure (vacuum) may be applied to the waste chamber 144. Both positive and negative pressures may be applied, in certain cases. Alternative fluid motive elements, such as one or more pumps, may be employed to control particle travel through opaque member 102.

Although both of supply chamber 142 and waste chamber 144 are illustrated as being open, it is within contemplation for one or both to be arranged to substantially contain the fluid sample within a plumbing device that includes a multilayer embodiment 140. Also of note, although a top-down fluid flow is illustrated in FIG. 2, fluid flow may be established in either direction through orifice 108. In one reverse-flow configuration, the positions of supply chamber 142 and waste chamber 144 would simply be reversed from their illustrated positions. In an alternative reverse-flow arrangement, the positions of the radiation source 104 and detector 106 would be reversed from their illustrated positions.

Figure 3:
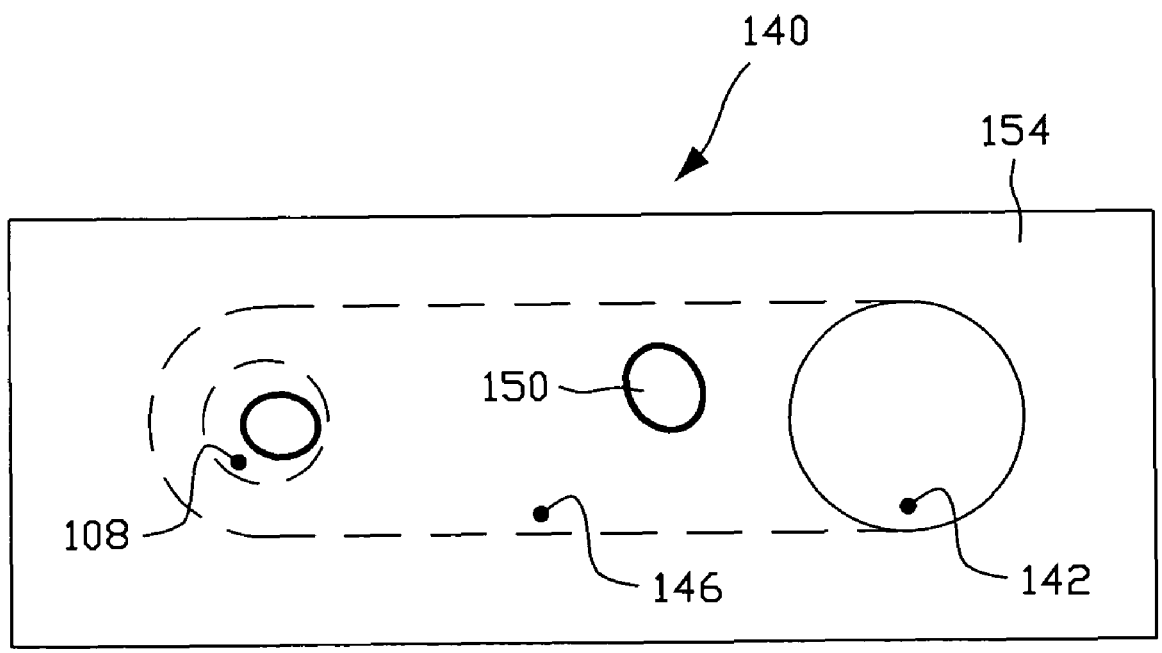
FIG. 3 is a top view of the plumbing arrangement illustrated in FIG. 2.

The multilayer plumbing arrangement 140 illustrated in FIGS. 2 and 3 includes a top cap layer 154, a top channel layer 156, an opaque member 102, a bottom channel layer 158, and a bottom cap layer 160. Such layers can be stamped, e.g. die cut, or manufactured by using a laser or water jet, or other machining technique, such as micro machining, etching, and the like. In a currently preferred embodiment 140 that is used to interrogate blood cells, the various layers are typically made from thin polymer films, which are then bonded together to form the multilayer assembly. Exemplary cap layers 154 and 160 may be manufactured from Mylar film that is preferably substantially clear or transparent.

During assembly of a device, bonding may be effected by way of an adhesive applied between one or more layer, or one or more layer may be self-adhesive. It is currently preferred for channel layers 156 and 158 to be manufactured from double-sided tape. One workable tape is made by Adhesive's Research (part no. AR90445). Heat and pressure may also be used, as well as other known bonding techniques. Desirably, the thickness of at least the channel layers 156, 158 is on the order of the characteristic size of particles of interest to promote single-file travel of particles through an interrogation zone. A workable thickness of such layers in currently preferred devices used to interrogate blood cells typically ranges between about 10 microns and about 300 microns.

In certain cases, at least a portion of bottom layer 160 is adapted to form a bottom window 162, through which radiation 118 may be transmitted into an excitation zone. Similarly, top layer 154 includes a portion forming a window 164, through which fluorescence may be transmitted. Therefore, the assembly 140 is arranged to form a window permitting radiation to pass through its thickness. Such window includes window portions 162, 164, certain portions of channels 146 and 148 disposed in the vicinity of orifice 108, and the orifice 108 itself. Radiation can therefore be directed through the thickness of the assembly 140 in the vicinity of the orifice 108.

Figure 4:
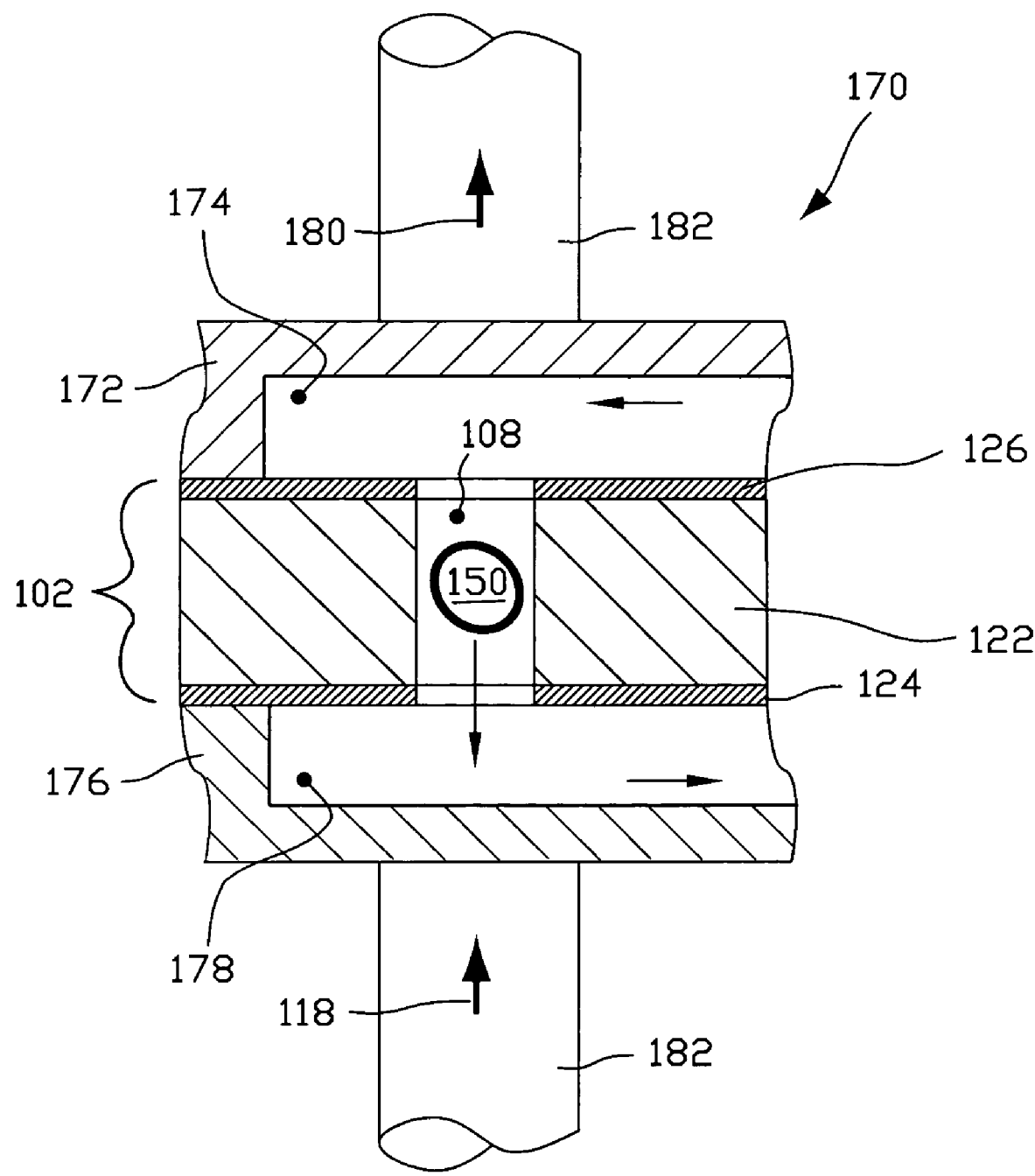
FIG. 4 is a cross-section in elevation illustrating certain details of another workable plumbing arrangement associated with certain structure of an interrogation platform.

The plumbing arrangement illustrated in FIG. 4, and generally indicated at 170, includes a top layer 172, which carries a carved-out fluid-flow channel 174. Bottom cap layer 176 similarly includes a carved-out channel 178. Carved-out channels may be formed, for example, by a known masking and chemical etching process. Opaque member 102 is adapted to dispose orifice 108 for fluid communication between channels 174 and 178. Bottom layer 176 is formed from a material that permits transmission of radiation in an appropriate spectrum to enable excitation of particles, which pass through an excitation zone associated with the orifice 108, by primary radiation 118. Top layer 172 is formed from a material that permits transmission of radiation in an appropriate spectrum to enable transmission of fluorescence 180 toward a radiation detector. Top layer 172 may also be adapted to resist transmission of primary radiation 118. Again, the fluid and particle flow may be in a direction reversed from that illustrated. As illustrated in FIG. 4, sometimes a plumbing arrangement, such as arrangement 170, may be coupled to, or associated with, a radiation source and/or a radiation detector by way of one or more fiber optic cable 182. A fiber optic cable 182 may be disposed to operate as a lens effective to capture a substantial portion of fluorescence transmitted through the plumbing arrangement 170. It should be noted that cables 182 are illustrated as being in contact with the top and bottom of assembly 170. However, such is not required.

Figure 5:
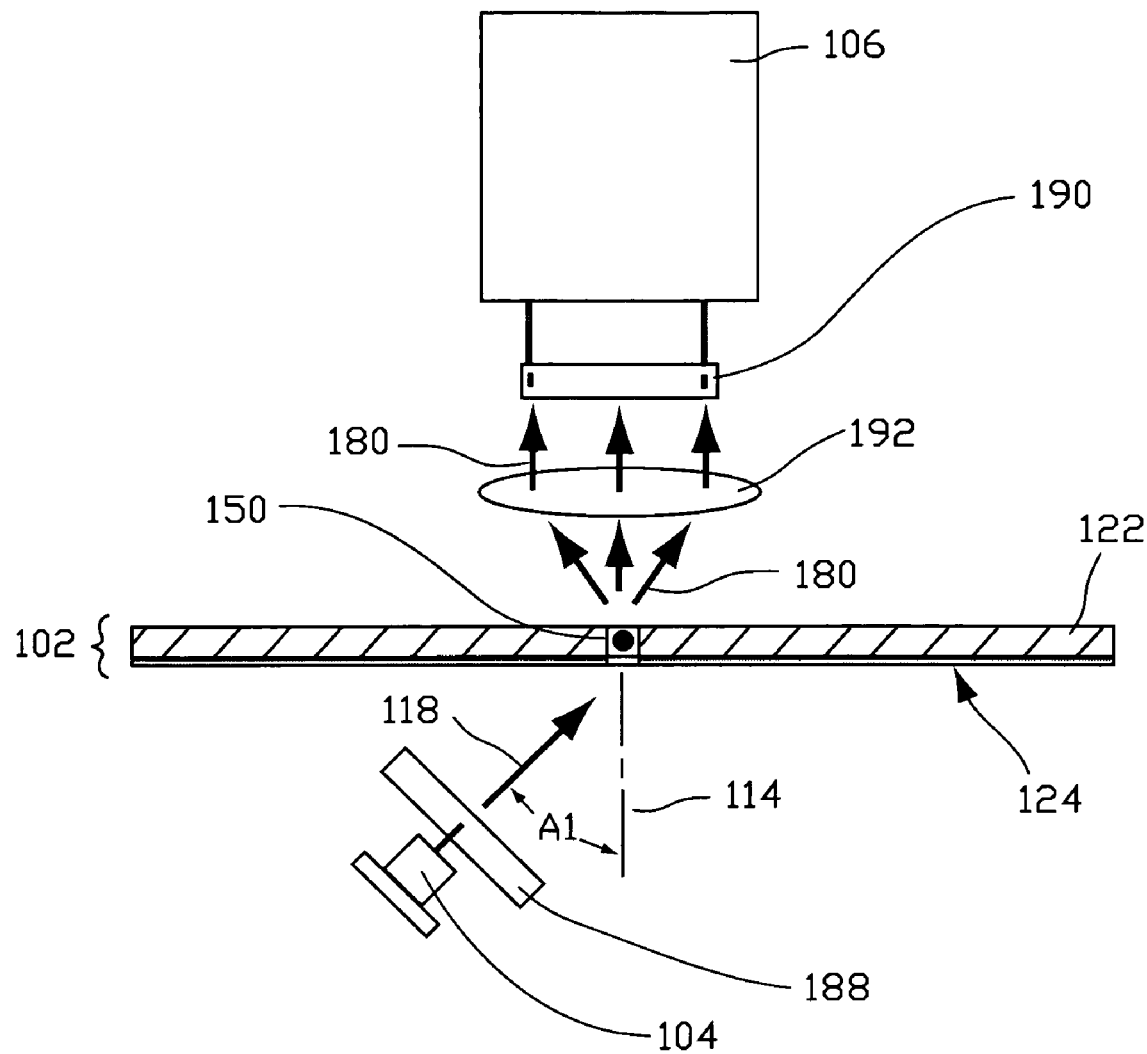
FIG. 5 is a view in elevation of a currently preferred arrangement for certain structure of an operable interrogation platform.

Because fluorescence propagates from a tagged and excited particle of interest in substantially all directions, the primary radiation may be directed to an excitation zone from a side, instead of only from directly below such zone. With reference now to FIG. 5, sometimes it is preferred to apply primary radiation 118 at an acute angle A1 to axis 114 of orifice 108. In such case, the opaque member 102 may even function substantially as an operable filter to resist direct transmission of primary radiation 118 to a radiation detector 106. As illustrated, radiation vector 118 can be oriented to pass through, or partially into, orifice 108 without being detected by radiation detector 106. However, when a tagged particle 150 is present in an excitation zone (such as orifice 108 as illustrated), the resulting fluorescence 180 may still be detected by the radiation detector 106. While a workable angle A1 may be between 0 and 90 degrees, it is currently preferred for angle A1 to be between about 15 and about 75 degrees for certain operable embodiments.

A radiation source 104 may be formed from a broad spectrum radiation emitter, such as a white light source. In such case, it is typically preferred to include a pre-filter 188 adapted to pass, or transmit, radiation only in a relatively narrow band encompassing the characteristic value required to excite a particular fluorescing agent associated with a particle of interest. It is generally a good idea to limit the quantity of applied radiation 118 that is outside the excitation wavelength to reduce likelihood of undesired saturation of the radiation detector 106, and consequent inability to detect particles of interest.

Certain embodiments apply a red diode laser, and include a short pass filter (after the diode laser) that passes primary light radiation with wavelengths shorter than 640 nm. Such embodiments also may include a band pass filter (prior to the photodetector) with a peak that matches a particular selected fluorescence peak. Commercially available dyes may be obtained having characteristic fluorescent peaks at 660, 694, 725, and 775 nanometers.

With continued reference to FIG. 5, sometimes it is preferred to include a post filter 190 that resists transmission of radiation outside the characteristic wavelength of the fluorescence 180. Such an arrangement helps to avoid false readings indicative of presence of a particle of interest in an excitation zone. Also, to assist in obtaining a strong signal, an optical enhancement, such as a lens 192, can be included to gather fluorescence 180 and direct such radiation toward the radiation detector 106. Illustrated lens 192 may be characterized as a convex focusing lens, and typically is disposed to focus on a point located inside the orifice 108.

Figure 6:
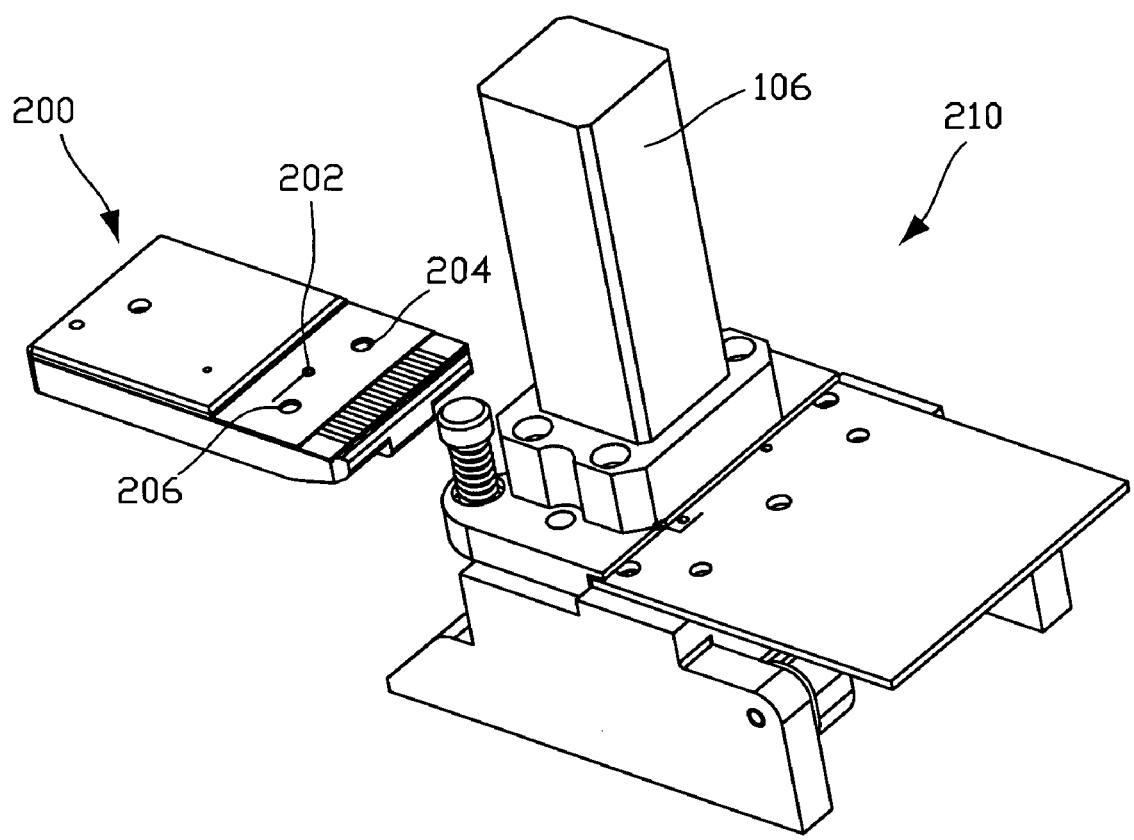
FIG. 6 is a perspective view from above of a workable interrogation platform and a removable cartridge carrying a plumbing arrangement.

With reference to FIG. 6, a plumbing arrangement, such as 140, 170, may be associated with a housing to form a cartridge assembly, generally indicated at 200. The cartridge may be configured to provide access through a radiation transmitting window 202 for purpose of exciting and detecting radiation. One or more fluid access ports 204, 206 may be provided to install a fluid sample into the cartridge 200, and to provide control over fluid motion through the cartridge 200. Such cartridge 200 can be configured to interface with holding structure of an interrogation platform, such as the interrogation platform generally indicated at 210, to associate the cartridge 200 in operable position with respect to interrogation equipment, such as detector 106, associated with the interrogation platform 210.

Figure 7:
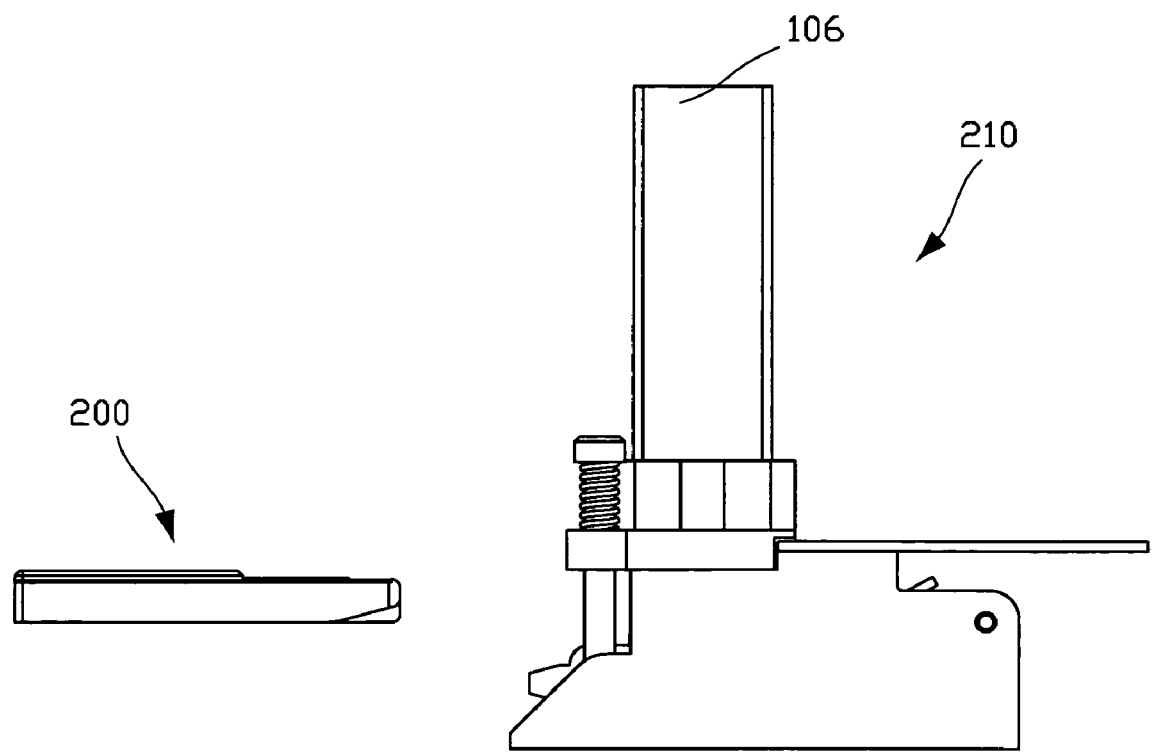
FIG. 7 is a side view in elevation of the structure illustrated in FIG. 6.
Figure 8:
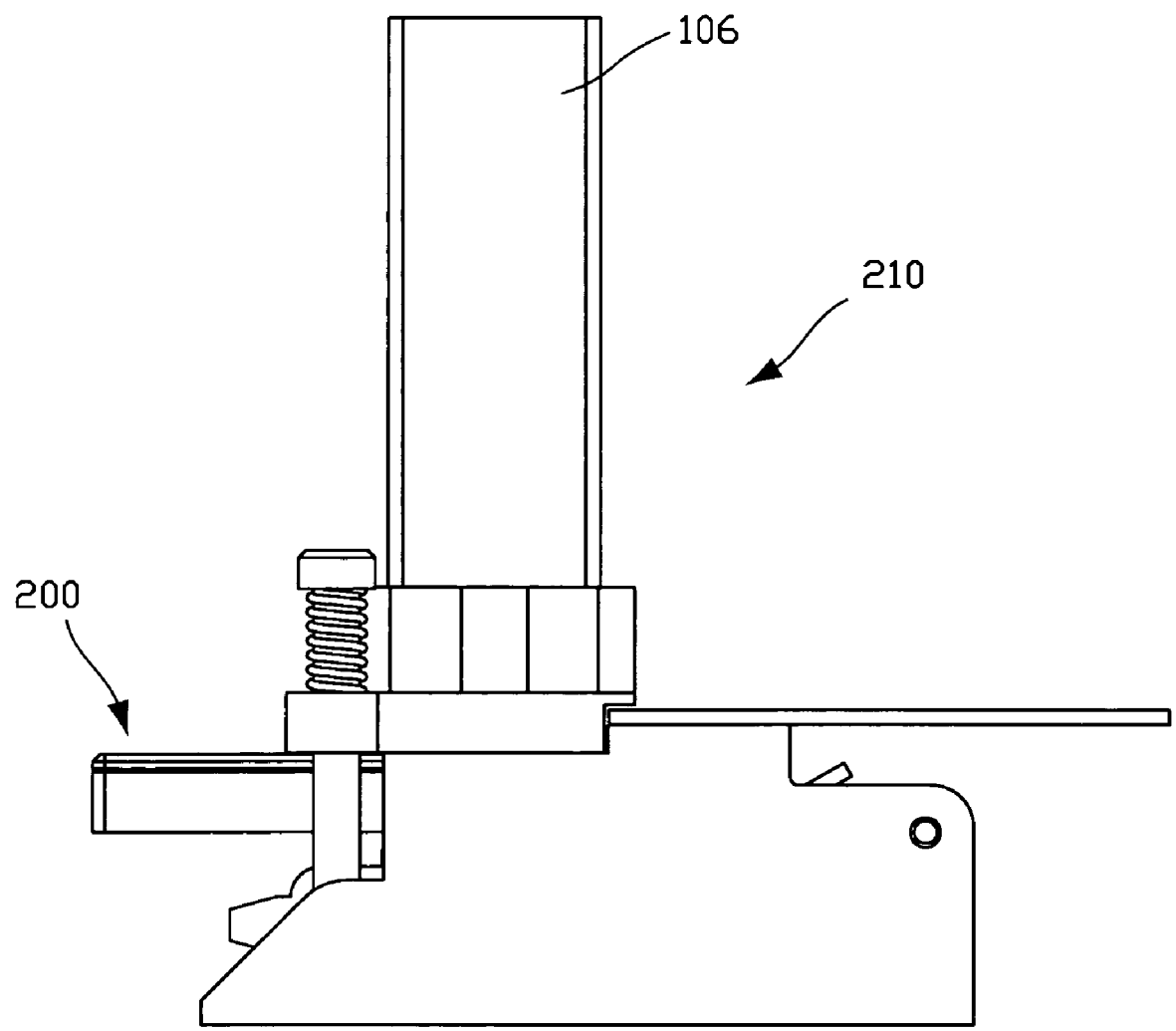
FIG. 8 is a side view in elevation of the structure illustrated in FIG. 6, with the cartridge seated in the interrogation platform.
Figure 9:
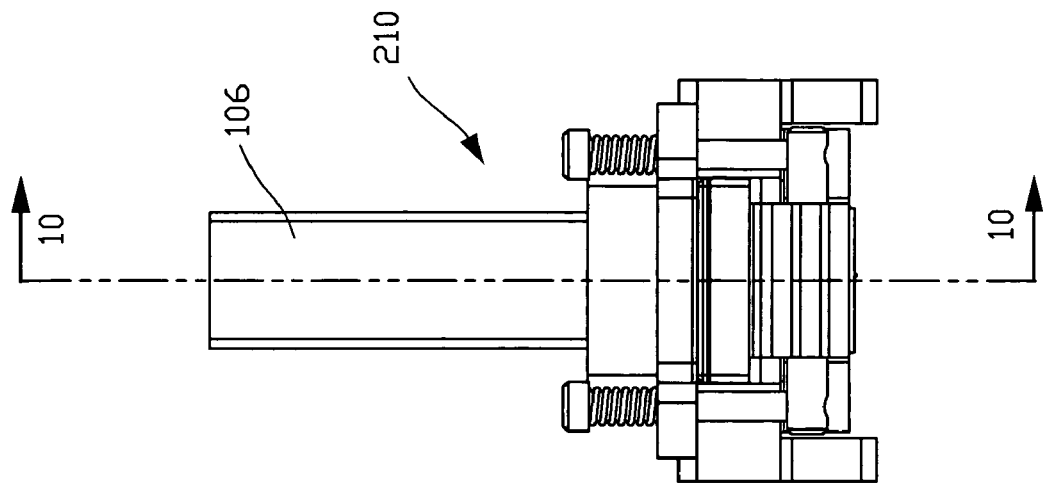
FIG. 9 is an end view in elevation of the structure illustrated in FIG. 6.
Figure 10:
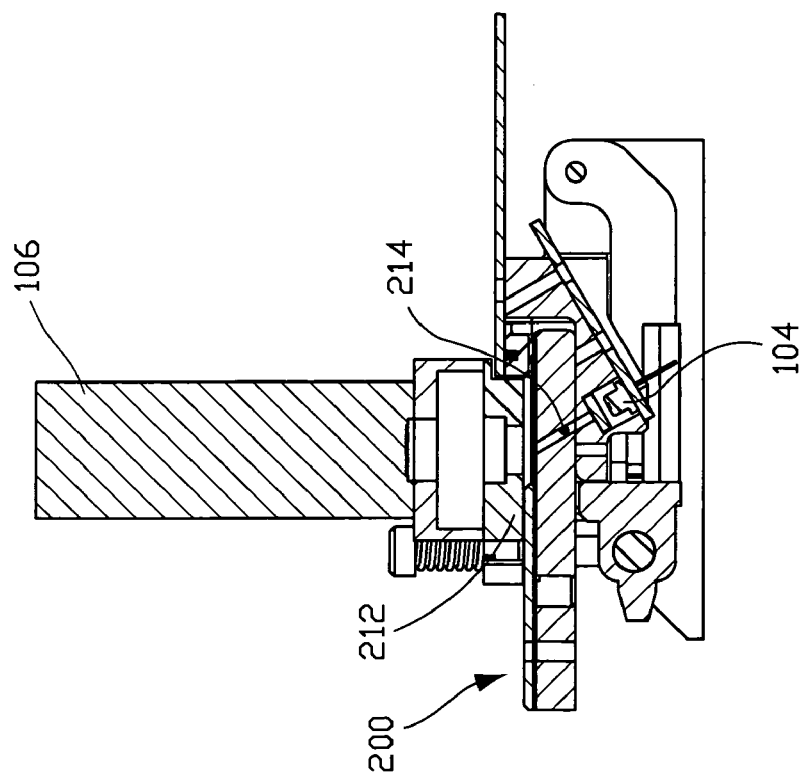
FIG. 10 is a cross-section view taken through section 10-10 in FIG. 9, and looking in the direction of the arrows.

FIG. 7 illustrates a cartridge 200 in position to slide into reception in holding structure of the platform 210. FIG. 8 illustrates cartridge 200 in an installed position in holding structure of the platform 210, and ready to perform an interrogation of particles of interest. FIGS. 9 and 10 cooperatively show details of a currently preferred platform 210. Cartridge 210 may be held in a test position by retaining structure, such as illustrated spring-loaded platen 212. The source of primary radiation 104 is disposed to emit primary radiation through tunnel 214 operably to radiate particles in an excitation zone of a plumbing arrangement (e.g. the plumbing arrangement that is embodied in cartridge 200). Radiation detector 106 is disposed to detect any resulting fluorescence.

Figure 11:
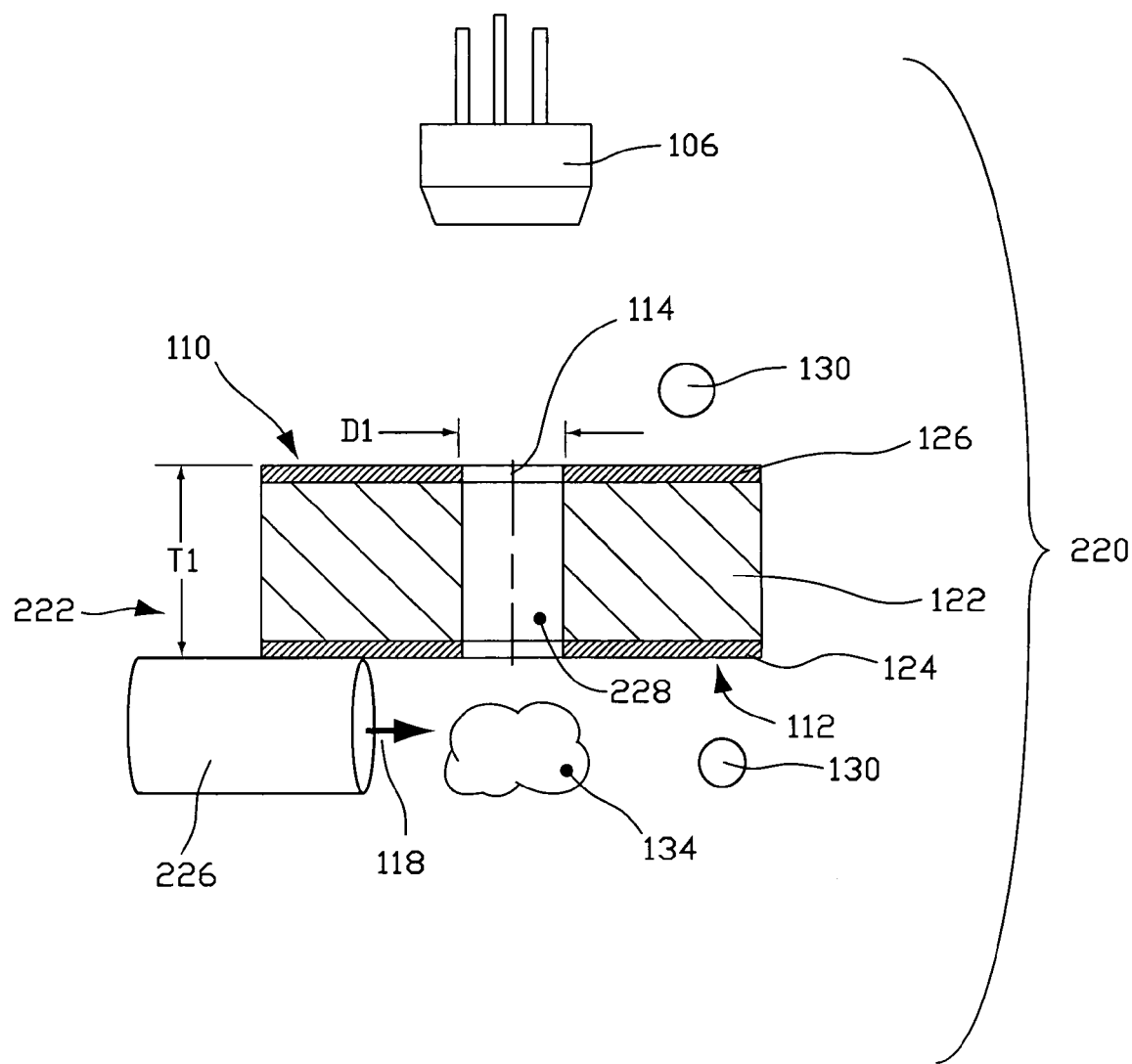
FIG. 11 is a schematic of a cross-section, similar to FIG. 1, taken through another embodiment illustrating general principles of operation of the invention.

With reference now to FIG. 11, a schematic illustrating a generalized operable arrangement employed in a currently more preferred embodiment structured according to certain principles of the invention is indicated generally at 220. As illustrated, embodiment 220 includes a barrier layer, generally indicated at 222, disposed between a radiation waveguide 226 and a radiation detector 106. In the currently most preferred embodiments, barrier layer 222 is at least substantially opaque to resist propagation of radiation there-through, in a thickness direction. An operable barrier layer 222 may be structured similar to opaque member 102, described above, and may therefore include one or more optional coating 124, 126. Alternatively, a bare core 122 may directly resist propagation of radiation there-through.

Waveguide 226 permits applied excitation radiation 118 to impinge on an interrogation zone, such as zone 134. An operable waveguide 226 may include a simple window, a fiber optic cable, or any structure capable of operating as a light pipe. For purpose of this disclosure, a light pipe may be defined as being capable of guiding radiation (e.g. light) along a curved path in space by enforcing propagation of radiation as a vector along a substantially proscribed path by way of a mechanism such as internal reflection. Sometimes, a waveguide 226 may alternatively be disposed on the same side of barrier layer 222 as the radiation detector 106. However, such is currently less preferred, as that configuration tends to cause a higher level of stray radiation that can be detected by detector 106. Such stray radiation is believed to increase background "noise" levels (measured by the photo detector 106) and thereby undesirably reduces the signal to noise ratio.

Desirably, at least one tunnel 228 is disposed in barrier layer 222 to provide an optical and fluid flow path between a first channel 174 (see FIG. 12), and a second channel 178. Tunnel 228 may be characterized as having a length-oriented through-axis 114 extending between the first and second sides 110 and 112 of barrier layer 222, respectively. It is within contemplation to provide a plurality of tunnels 178 to permit parallel interrogation of particles through redundant interrogation zones. Such plurality of tunnels resists scrapping a test due to a clogged tunnel, and may provide more rapid test turn-around. It is within contemplation to account for simultaneous fluorescence signals being detected from parallel interrogation zones (for non-limiting example) by incorporating intensity of the signal(s) received by detector 106 into data manipulation procedures.

It is generally desirable for structure associated with any or all of first fluid channel 174, tunnel 228, and/or second fluid channel 178 to be configured as organizing structure effective to urge particles into substantially single-file travel through an interrogation zone, such as interrogation zone 134. One exemplary organizing structure effective to cause substantially single-file travel of particles in an apparatus used to detect certain blood cells includes a tunnel 228 having a characteristic size of about 5 to about 10 times the diameter of a blood cell of interest. Furthermore, the upstream and downstream channels (in the vicinity of the tunnel of such embodiment) typically may have a cross-section on the order of about 25 times the size of the tunnel cross-section. Also, dilution of the particles in a fluid carrier may contribute to organizing particle travel. As a non-limiting example, it is currently preferred to interrogate fluid samples having a particle density of approximately between about $3\times10^3$ to about $3\times10^5$ cells/ml, where the particle size is on the order of the size of a red blood cell.

Certain currently preferred embodiments apply stimulation radiation 118 as a vector directed substantially transverse to the direction of fluid flow caused by structure configured to urge particles into a desired substantially single-file arrangement. While the embodiment illustrated in FIG. 11 delivers stimulation radiation via a fiber optic cable, it is within contemplation to provide alternative structure effective to guide the direction of applied stimulation radiation 118. For example, with reference to FIG. 12, stimulation radiation 118 applied out-of-plane to a layer in a multilayered interrogation device may encounter a reflective element, generally indicated at 230 (e.g. a mirror element or reflective facet, such as a polished edge), arranged to direct stimulation radiation from a conveniently applied direction of radiation propagation to the preferred direction substantially transverse to fluid flow urged by organizing structure such as tunnel 228. Therefore, sometimes a layer itself may even operate as a radiation waveguide by being structured to partially, or totally, reflect radiation by internal reflection within the layer. A portion of a light pipe may be configured to focus, or otherwise gather, radiation from a first area of applied radiation to a smaller discharge area effective to impinge a desired intensity of applied stimulation radiation onto an interrogation zone.

Figure 12:
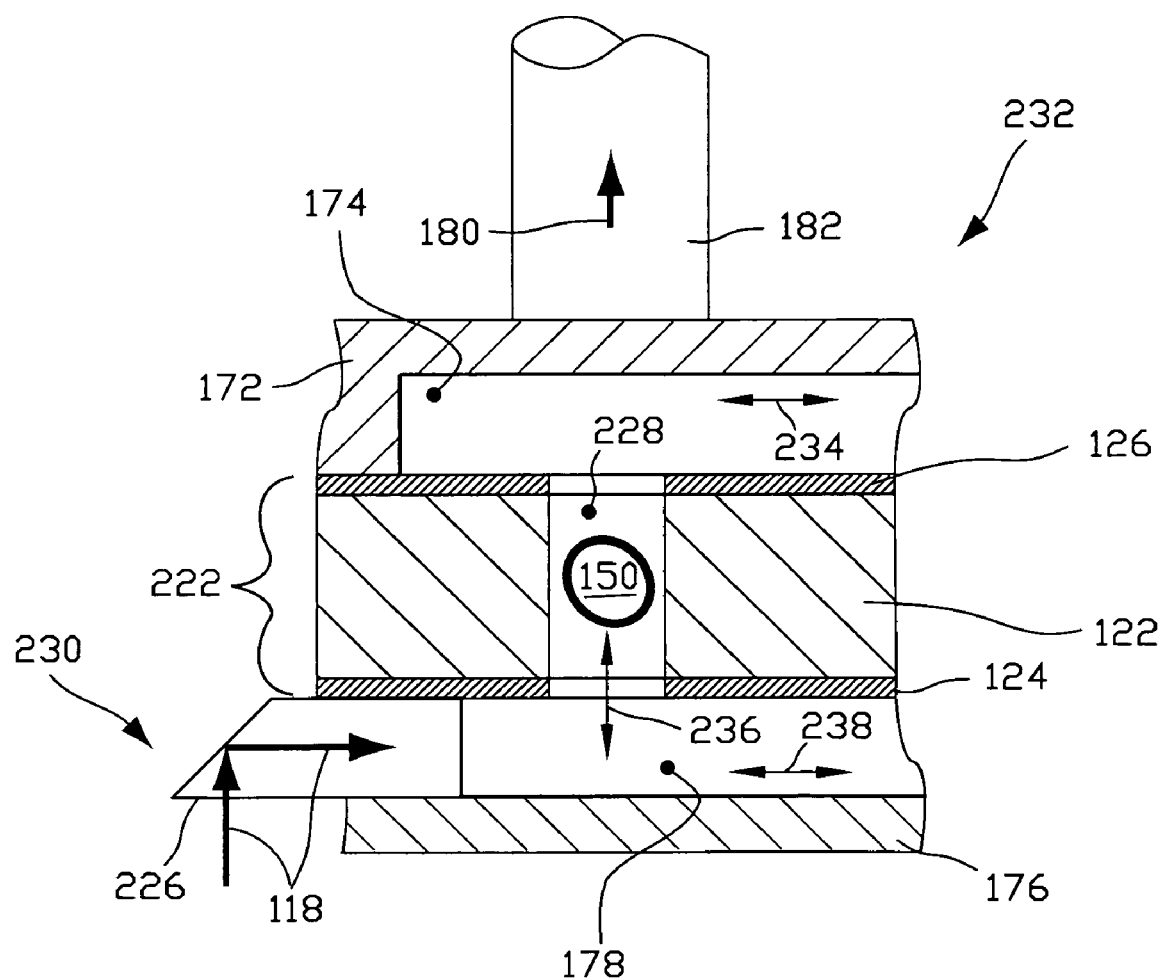
FIG. 12 is a cross-section in elevation, similar to FIG. 2, illustrating certain details of an alternative workable plumbing arrangement that may be associated with certain structure of an interrogation platform.

Fluid flow through an exemplary embodiment will now be characterized with further reference to the alternative plumbing arrangement generally indicated at 232 in FIG. 12. It should be noted that flow of particles 150 may be in either direction along a channel 174, 178, or through tunnel 228. Such operable flow directions are indicated by double-headed arrows 234, 236, and 238, respectively. It is recognized that there is an area of transition in flow direction at the junction between a channel 174, 178 and the tunnel 228. However, for purpose of this disclosure, and particularly in the context of claim construction, fluid flow may be characterized in more simple terms. For example, illustrated fluid flow 236 along an axis through tunnel 228 is defined as being directed approximately orthogonal to fluid flow 234, which is directed along an axis of a portion of channel 174 disposed adjacent to tunnel 228. Also, illustrated fluid flow 236 along an axis through tunnel 228 is also defined as being directed approximately orthogonal to fluid flow 238, which is directed along an axis of a portion of channel 178 disposed adjacent to tunnel 228. Therefore, it may be fairly characterized that the tunnel 228 causes a local change in direction of fluid flow through a lumen that includes channels 174, 178.

Figure 13:
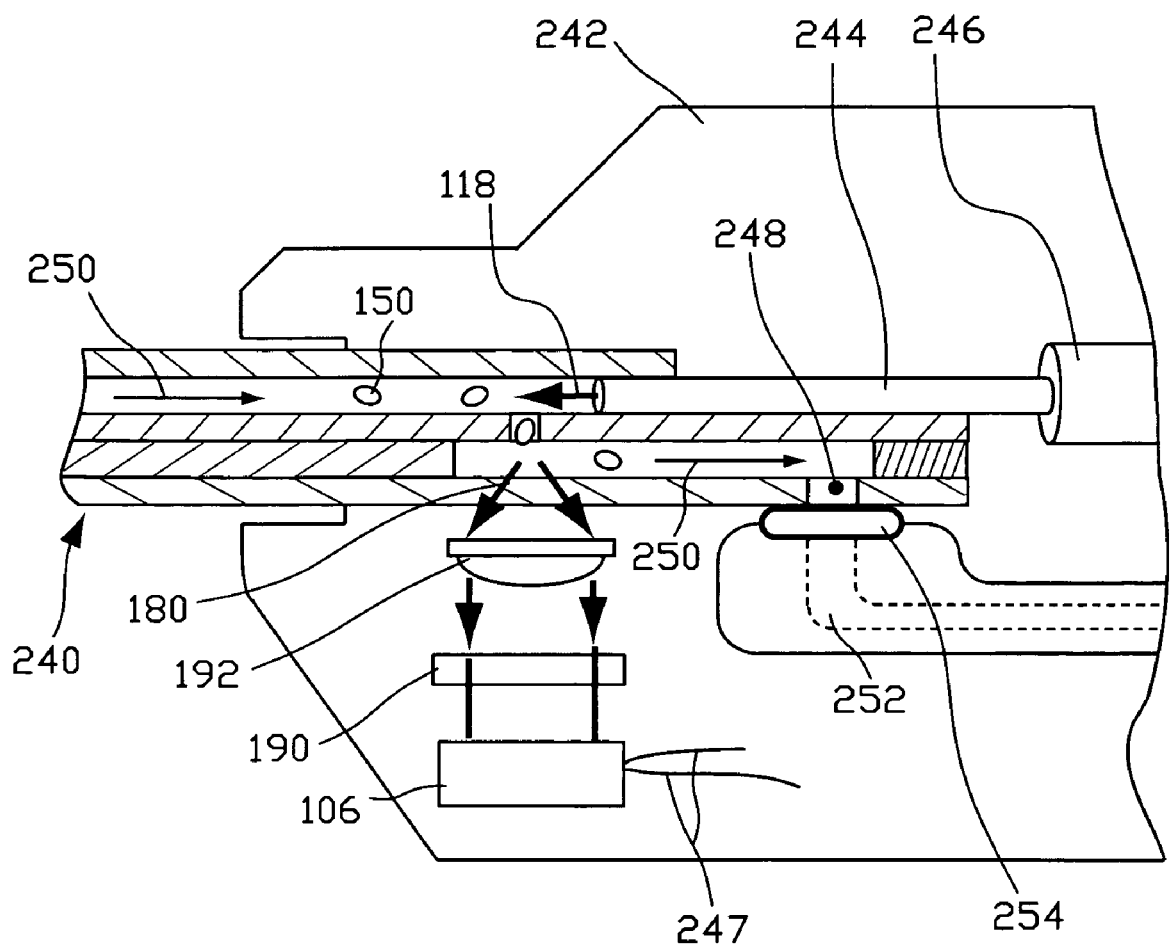
FIG. 13 is a cross-section in elevation, similar to FIG. 12, illustrating certain details of an alternative workable plumbing arrangement in association with a portion of an interrogation platform.

With reference now to FIG. 13, an exemplary plumbing arrangement effective to interrogate particles 150 entrained in fluid is indicated generally at 240. The interrogation arrangement 240 is illustrated in an installed position with respect to an interrogation platform 242. A workable interrogation platform 242 may be embodied in various forms, for example as a bench-top device, or a hand-held instrument, such as a hand-held pipette adapted to extract one or more sample from a bulk container of fluid.

Desirably, coupling the interrogation arrangement 240 to the interrogation platform 242 also places a waveguide, such as light pipe 244 (which, for example, may be a fiber optic cable), into communication with a radiation source. An operable coupling may either be done in "free space" by simply shining the laser into a fiber (or waveguide), or by butt-coupling two fibers together. The radiation source, such as a laser, can be located at virtually any convenient location in the interrogation platform when using the butt-coupling approach.

Figure 14:
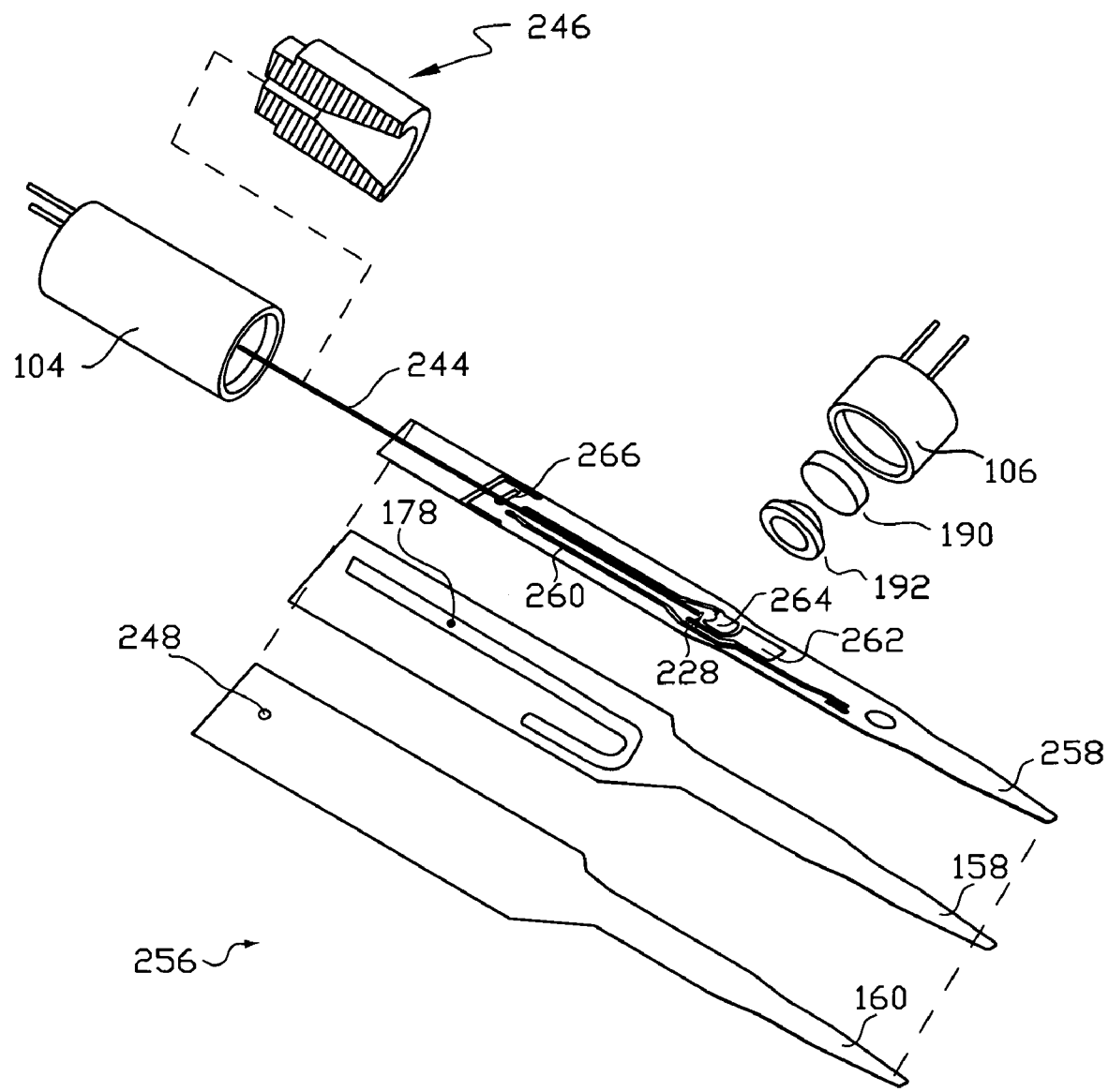
FIG. 14 is a view in perspective, partially exploded, of an electrically instrumented opaque member of a plumbing arrangement in operable association with a radiation source and a detector.

As illustrated in FIGS. 13 and 14, an end of light pipe 244 may be engaged by coupling device 246 upon insertion of arrangement 240 into seated engagement in platform 242. Coupling device 246 is structured to orient the end of light pipe 244 in an operable receiving position with respect to radiation provided by a radiation source 104. Therefore, excitation radiation 118 may be impinged onto an interrogation zone, causing emission radiation 180 from particles of interest to propagate toward a radiation detector 106. In an alternative interrogation platform, coupling 246 may place a fiber optic cable (e.g. extending from a more remotely located radiation source) into communication with a light pipe 244, or other waveguide associated with an interrogation arrangement.

Of note, radiation detector 106 may be disposed in proximity to the interrogation site, as perhaps suggested by FIG. 13. In such case, wires 247 typically extend from detector 106 to remotely located data collecting devices. Alternatively, radiation detector 106 may be located at a more convenient remote location of the interrogation platform 242, and radiation 180 may be communicated to such remote location by way of a light pipe. As previously indicated, sometimes a focusing element 192, and/or a filter 190 may be included to modify radiation that is transmitted toward detector 106, if desired.

Also as illustrated in FIG. 13, coupling the interrogation arrangement 240 to the platform 242 desirably places a source of suction into fluid communication with flow aperture 248 to cause a desired flow of sample fluid through interrogation arrangement 240, indicated by arrows 250. In the exemplary illustrated embodiment, a source of suction (not illustrated) communicates through passageway 252, which is in sealed communication through an O-ring 254 to aperture 248.

With reference again to FIG. 14, sometimes a plumbing arrangement operable to interrogate particles radiologically may also include structure adapted to interrogate a fluid sample in one or more alternative way. For example, one or more electrodes may be carried by a plumbing arrangement and arranged to permit interrogation of one or more electrical property related to a fluid sample. The partially exploded plumbing arrangement of a disposable embodiment generally indicated at 256 includes an opaque layer 258 that carries a plurality of electrically conductive traces (e.g. trace 260). It should be recognized that layers 158 and 160 are illustrated as being slightly distorted (stretched) to provide clarity as to indicated structure. The conductive traces are configured and arranged to form interrogating electrodes (e.g. 262, 264, 266) that are in electrical communication with connection electrodes (e.g. generally indicated at 268 in FIG. 15).

Embodiment 256 exemplifies a multifunction pipette tip that is configured to incorporate both electrical and radiological interrogation of fluid in a single disposable device. Illustrated embodiment 256 is a multilayer device structured somewhat similarly to a combination of embodiment 140 in FIG. 2 and embodiment 232 in FIG. 12. As pipette tip 256 is coupled to a pipette (not illustrated), light pipe 244 is directed by the internally conic section of coupling 246 effective to align a proximal end of light pipe 244 with a discharge from radiation source 104. A fully installed tip 256 automatically has its light pipe 244 positioned to receive radiation from source 106. Stimulation radiation (light) may then be applied along light pipe 244 to impinge on an interrogation zone associated with the tunnel generally indicated at 228. Further, coupling pipette tip 256 with a pipette also desirably places a vacuum source into communication with flow aperture 248.

Also, surface contact electrodes (disposed on the side facing away for the illustrated embodiment 256) are desirably placed into electrical communication with electrical interrogation circuitry when the pipette tip 256 is seated in an electrically instrumented pipette. Among other uses (such as direct particle counting using measured impedance and the Coulter principle), the electrodes may be arranged to indicate presence of a fluid wave-front at particular locations along a channel, such as a portion of channel 178. In a preferred arrangement, one or more electrode(s) may be arranged to start and stop a test based upon a feedback obtained from the electrode(s).

In general, some sort of feedback signal can be used to indicate a start condition for a test of a fluid sample (e.g. a signal may be generated electrically or optically to detect the fluid wave-front at a known location along a channel). Similarly, some sort of feedback signal can be used to indicate a stop condition for a test on a sample (e.g. electrically or optically detect the wave-front after filling a desired/known volume. Alternatively, a vacuum shut-off signal may be generated by monitoring amperage of the vacuum pump, which may spike when fluid flow terminates by fluid encountering a barrier at the end of a known-volume chamber that resists fluid flow but permits passage of air).

With reference still to FIG. 14, an electrode (e.g. 262) may be desirably disposed to indicate the presence of a fluid wave front at the beginning of a length of channel defining a chamber having a known volume corresponding to a desired sample volume size. The signal monitored at electrode 262 may provide a useful start-test signal. A second electrode (e.g. 266) may be disposed at the other end of the known-volume chamber to provide a stop-test signal. A discontinuous change in impedance measured at an electrode (essentially changing from open-circuit to a measurable value as an electrolytic fluid closes the circuit) can be used to indicate arrival of the fluid wave-front. Such start- and stop-signals may be used to advantage to substantially automate data collection during radiological tests of fluid samples.

Figure 15:
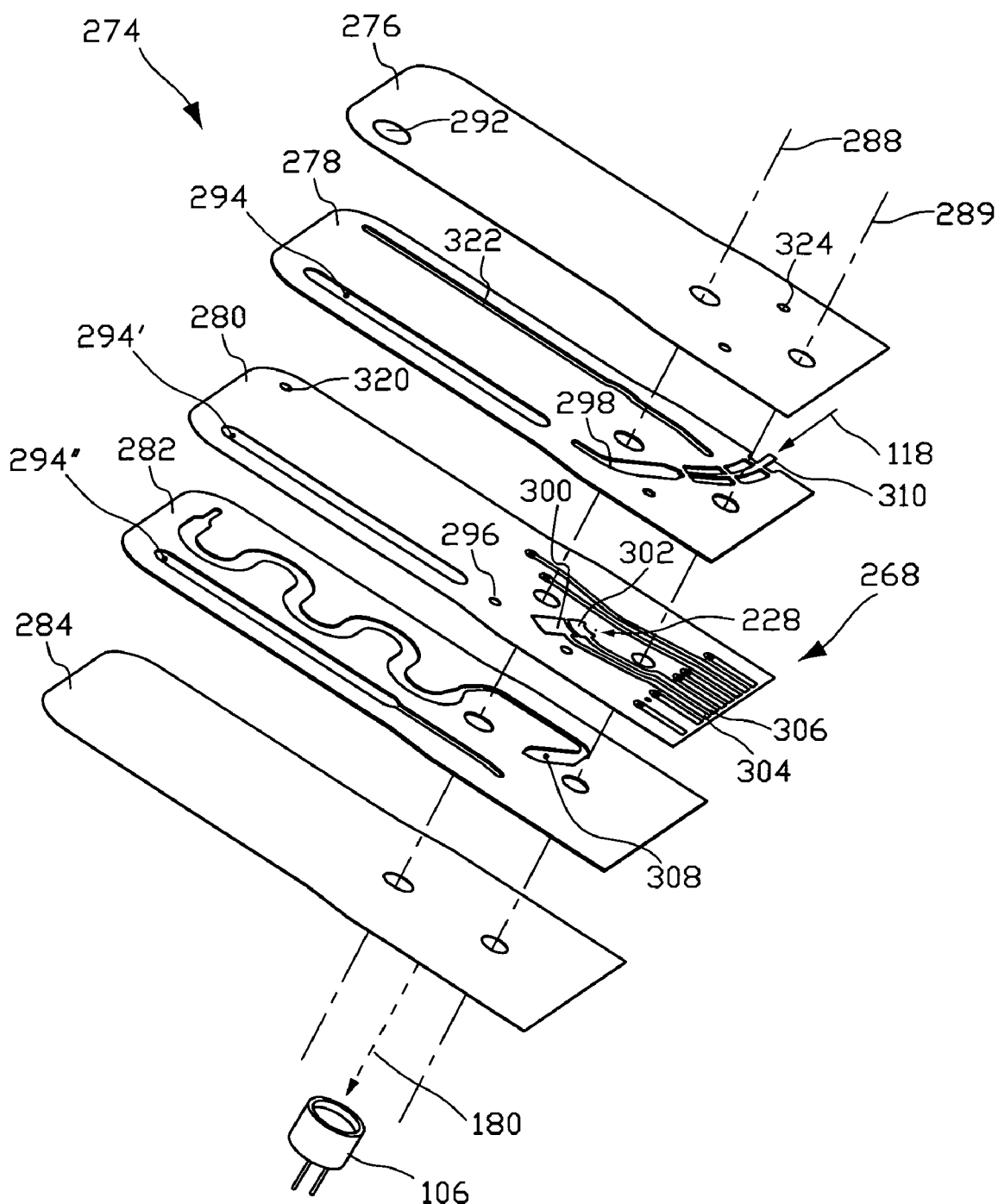
FIG. 15 is an exploded assembly view in perspective of a workable plumbing arrangement to interrogate particles radiologically and/or electrically.
Figure 16:
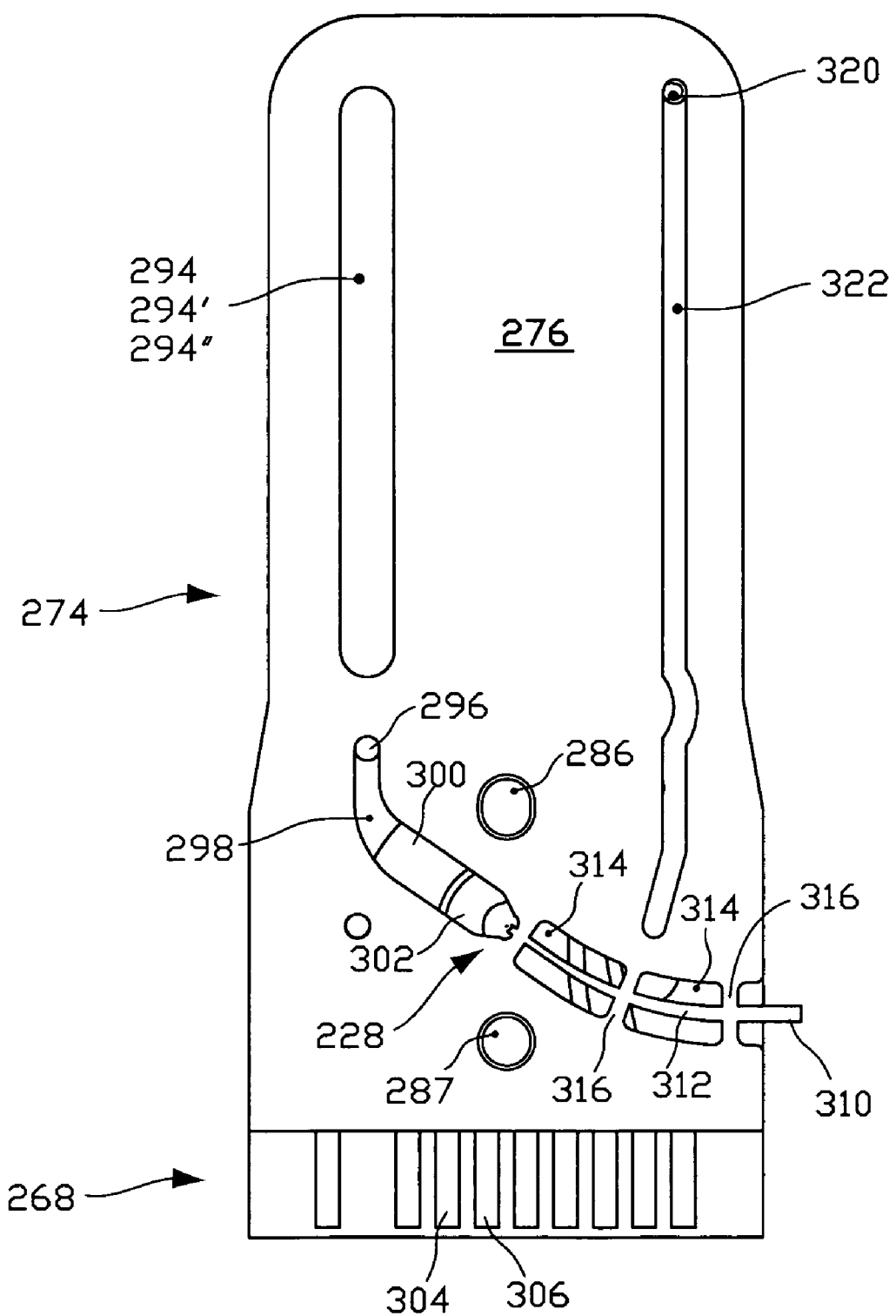
FIG. 16 is a top view of the assembly illustrated in FIG. 16.

Another embodiment permitting either radiological and/or electrically based interrogation of a fluid sample is indicated generally at 274 in FIGS. 15 and 16. Device 274 is particularly adapted as a disposable cartridge for use in combination with a bench-top interrogation platform. As illustrated, device 274 is formed from a plurality of layers, including cap layer 276; channel layer 278, opaque layer 280; channel layer 282, and cap layer 284. Alignment structure, including apertures 286 and 287, facilitates assembly of device 274 by guiding constituent parts along center lines 288 and 289. In currently preferred embodiments, device 274 is made from layers of thin film, as previously described. Sometimes, one or more layer may be formed from a material, such as injection molded plastic, having an increased thickness to provide enhanced bending stiffness to facilitate handling of the device 274, provide one or more larger known-volume chamber, or for other reasons.

In use of device 274, the device is inserted into engagement in an interrogation platform configured to provide the appropriate and desired interrogation capabilities. An interrogation platform typically includes a vacuum source, and one or both of electrical and radiological instrumentation. A fluid sample is placed into sample well 292, where it flows into a chamber defined by chamber-forming voids 294, 294', and 294". The fluid is then drawn from channel 294" through aperture 296 in layer 280, and into channel 298 in layer 278. As illustrated, fluid in channel 298 flows in succession over interrogation electrodes 300 and 302. With particular reference to FIG. 15, it can be seen that the trace forming interrogation electrode 300 also forms connection electrode 304. Similarly, the conductive trace forming interrogation electrode 302 also forms connection electrode 306.

After passing interrogation electrodes 300 and 302, fluid flows downward, through tunnel 228, to channel 308 in layer 282. Additional interrogation electrodes are typically disposed for contact with fluid in channel 308. Such interrogation electrodes may be used, for examples, to interrogate particles moving through tunnel 228 using electrical impedance and the Coulter principle, and/or as start and/or stop trigger(s) for interrogating a predetermined volume of fluid.

As particles move past the tunnel 228, they may also, or alternatively, be interrogated radiologically at an interrogation zone generally associated with tunnel 228. Stimulation radiation 118 may be introduced to a waveguide through pigtail 310. With particular reference to FIG. 16, an exemplary and operable waveguide includes a sidewalk 312 formed by voids 314 formed in a layer. Pillars 316 are provided in the illustrated embodiment 274 to provide stability for sidewalk 312 during assembly of the cartridge 274. The waveguide formed by sidewalk 312 is further exemplary of a focusing light pipe, in which a cross-section of sidewalk 312 is configured to focus radiation transmitted there-through for impingement of focused radiation on an interrogation zone at an increased intensity compared to an intensity of "upstream" radiation, such as radiation received across a transmission interface of the pigtail 310.

Making reference again to FIG. 15, subsequent to filling channel 308, fluid passes through aperture 320, in layer 280, to channel 322 in layer 278. Aperture 324 is provided through layer 276 to permit application of a desired fluid-motive vacuum to channel 322.

An operable plumbing arrangement structured according to certain principles of the instant invention may be manufactured using the following procedure: 1. Lay fiber down sandwiched into one of the layers of tape (i.e. laminate). The layer the fiber is integrated into will typically have a receiving channel that is cut and sized for the fiber. 2. Additional laminate layers, or adhesive, may be added to keep the fiber in position. 3. The sub-assembly may then be sent to a laser drilling house to drill the cell sensing zone (CSZ) hole through the opaque layer. The hole will desirably be drilled relative to the location of the fiber (i.e., just off the end of the tip of the fiber). 4. The assembly is then typically finished when the final laminate cap layers (typically clear Mylar layers) are added.

Certain components that are operable to construct an apparatus according to certain principles of the instant invention are commercially available. For example, one operable source of radiation 104 includes a red diode laser available under part number VPSL-0639-035-x-5-B, from Blue Sky Research, having a place of business located at 1537 Centre Point Drive, Milpitas, Calif. 95035. Filter elements 188, 190 are available from Omega Optical, having a place of business located at 21 Omega Dr., Delta Campus, Brattleboro, Vt. 05301. Preferred filters include part numbers, 660NB5 (Bandpass filter), and 640ASP (shortpass filter). An operable radiation detector 106 includes a photomultiplier tube available from the Hamamatsu Corporation, having a place of business located at 360 Foothill Rd., Bridgewater, N.J. 08807, under part number H5784-01. Molecular Probes (a division of Invitrogen Corporation, www.probes.invitrogen.com) supplies a plurality dyes that are suitable for use in tagging certain particles of interest for interrogation using embodiments structured according to the instant invention. In particular, AlexaFluor 647, AlexaFluor 700, and APC-AlexaFluor 750 find application to interrogation of blood cells. These dyes are also commonly used in flow cytometric applications and have specific excitation and emission characteristics. Each dye can be easily conjugated to antibodies for labeling, or tagging, different cell types. An operable fiber optic cable for forming a waveguide is available under part No. BK-0100-07 from Thor Labs, having a web site address of http://www.thorlabs.com. One useful fiber diameter is about 0.010".

In one method for using the invention, particles (e.g. blood cells) of interest are mixed with a commercially available (i.e., obtained from Invitrogen Corporation, Carlsbad, Calif.) or custom manufactured antibody-bound fluorescently labeled molecules. The mixture is then incubated for a brief period of time (approximately 5 to 15 minutes) at a temperature typically between about room temperature and abut 39 degrees Celsius. For preparation of white blood cells for interrogation, a small amount of fluorescent dye (e.g. 10 microliters) is added to about 10 microliters of whole blood, vortexed and then incubated for about 15 minutes at room temperature in the dark. A lysing agent is then added to lyse the red blood cells. Once added, the mixture is again vortexed and then allowed to incubate for another 15 minutes (in the dark).

Fluorescent markers bind to cells (or other particles of interest) in the sample during the incubation period. The particles suspended in solution are then passed through the orifice detection zone from one (supply) reservoir to another (waste) reservoir, typically by applying either an external vacuum source to pull the sample through or an external positive gas source to push the sample through. Fluorescently labeled particles are excited with primary radiation (light) as they traverse the opaque member (through the orifice) which causes fluorescence and subsequent emission of light having a secondary wavelength (which is released into the opposite or detector side of the opaque member). Particles flow away from the detection orifice to a waste reservoir or storage containment area.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for detecting a Stokes-shift caused by certain particles entrained in a fluid, the apparatus comprising:
   a first fluid channel;
   a second fluid channel;
   a barrier layer disposed between said first fluid channel and said second fluid channel, a first tunnel extending through said barrier layer permitting fluid communication between said first fluid channel and said second fluid channel;
   an interrogation zone associated in proximity to said first tunnel;
   a first optical path configured to admit excitation-radiation to said interrogation zone; and
   a second optical path configured to permit propagation of emission-radiation, from a particle of interest disposed in said interrogation zone and stimulated by said excitation-radiation, toward a radiation-detection device, wherein:
   structure associated with any or all of said first fluid channel, said first tunnel, and/or said second fluid channel is configured to urge substantially single-file travel of particles through said interrogation zone.

2. The apparatus according to claim 1, wherein:
said barrier layer is substantially opaque to radiation.

3. The apparatus according to claim 1, wherein:
said first optical path is configured to guide said stimulation-radiation to impinge on said interrogation zone at an angle substantially transverse to an axis of said tunnel.

4. The apparatus according to claim 1, wherein:
said apparatus is structured effective to permit either of, or both of:
   1) radiological interrogation of a portion of said fluid as said portion flows through said interrogation zone, and
   2) interrogation of an electrical property associated with said fluid as said fluid flows through either, or both, of said first fluid channel and said second fluid channel.

5. The apparatus according to claim 1, wherein:
said apparatus is configured and arranged to provide:
   a first feedback signal to indicate a start condition for an optical interrogation test of a portion of said fluid as said portion flows through said interrogation zone; and
   a second feedback signal to indicate a stop condition for said optical interrogation test.

6. The apparatus according to claim 1, wherein:
said first optical path comprises a portion of a light pipe carried by said apparatus.

7. The apparatus according to claim 6, wherein:
said light pipe is configured to focus radiation transmitted there-through for impingement of focused radiation on an interrogation zone at an increased intensity compared to an intensity of radiation received at a transmission interface of said light pipe.

8. The apparatus according to claim 6, wherein:
a pig-tail portion of said light pipe extends from a perimeter of said apparatus to permit coupling a source of radiation to said pig-tail.

9. The apparatus according to claim 1, wherein:
said second optical path comprises at least a portion of said first tunnel.

10. The apparatus according to claim 1, wherein:
said first optical path directs excitation-radiation toward one side of said barrier layer; and
said second optical path is configured to permit emission-radiation to propagate from the other side of said barrier layer toward a radiation-detection device.

11. The apparatus according to claim 1, wherein:
said apparatus comprises a multilayered, thin film, microfluidic plumbing arrangement.

12. The apparatus according to claim 1, wherein:
said apparatus comprises a plurality of thin film layers, said first fluid channel being disposed in a first layer, and said second fluid channel being disposed in a second layer.

13. The apparatus according to claim 1, wherein:
fluid flow along an axis through said tunnel is directed approximately orthogonal to fluid flow along an axis of a portion of said first channel disposed adjacent to said tunnel.

14. The apparatus according to claim 13, wherein:
fluid flow along an axis through said tunnel is also directed approximately orthogonal to fluid flow along an axis of a portion of said second channel disposed adjacent to said tunnel.

15. The apparatus according to claim 1, wherein:
said first tunnel has a characteristic dimension sized between about 5 microns and about 200 microns.

16. The apparatus according to claim 1, wherein:
a thickness of said barrier layer is between about 10 microns and about 300 microns.

17. The apparatus according to claim 1, further comprising:
a first filter disposed between a radiation source and said radiation-detection device, said first filter being configured and arranged to resist reception of said stimulation-radiation by said radiation-detection device.

18. An apparatus for detecting a Stokes-shift caused by certain particles entrained in a fluid, the apparatus comprising:
   a first thin film layer defining a first fluid channel;
   a second thin film layer defining a second fluid channel;

a third thin film layer structured to be substantially opaque to radiation propagation there-through in a thickness direction and disposed between said first thin film layer and said second thin film layer, a tunnel extending through said third thin film layer permitting optical and fluid communication between said first fluid channel and said second fluid channel;

an interrogation zone associated in proximity to said tunnel, wherein:

structure associated with any or all of said first fluid channel, said tunnel, and/or said second fluid channel is configured to urge travel through said interrogation zone of particles in substantially single-file;

a first optical path configured to admit excitation-radiation, from an external radiation source, to said interrogation zone; and a second optical path configured to permit propagation of emission-radiation, from a particle of interest disposed in said interrogation zone and stimulated by said excitation-radiation, to the exterior of said apparatus.

19. The apparatus of claim 18, wherein:

said first optical path comprises a radiation waveguide configured to direct said stimulation-radiation to impinge on said interrogation zone at an angle substantially transverse to an axis of said tunnel.

20. The apparatus according to claim 18, wherein:

said thin film layers are carried on a removable and disposable cartridge, said cartridge being adapted to interface with structure of an interrogation platform, and in combination with:

said interrogation platform, wherein:

said interrogation platform comprises:

said radiation source;

a radiation detector; and structure operable to apply a motive force to fluid effective to cause fluid flow through said interrogation zone.

* * * * *